United States Patent [19]

Sarantakis

[11] Patent Number: 4,487,716

[45] Date of Patent: Dec. 11, 1984

[54] N-(1-CARBOXY-3-PHENYLPROPYL)-DIPEPTIDES

[75] Inventor: Dimitrios Sarantakis, West Chester, Pa.

[73] Assignee: American Home Products Corporation, New York, N.Y.

[21] Appl. No.: 410,665

[22] Filed: Aug. 23, 1982

[51] Int. Cl.³ ............................................ C07C 103/52
[52] U.S. Cl. ............................................ 260/112.5 R
[58] Field of Search ............................ 260/112.5 R

[56] References Cited

FOREIGN PATENT DOCUMENTS 12401   6/1980  European Pat. Off. ..... 260/112.5 R
2095682 10/1982 United Kingdom ......... 260/112.5 R

OTHER PUBLICATIONS

Patchett et al., Nature, 288, 280–283 (1980).

Primary Examiner—Delbert R. Phillips
Attorney, Agent, or Firm—Richard K. Jackson

[57] ABSTRACT

The N-(1-carboxy-3-phenylpropyl)-dipeptides of the formula:

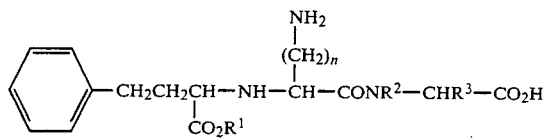

inhibit angiotensin converting enzyme and serve as antihypertensive agents to reduce blood pressure in animals.

5 Claims, No Drawings

N-(1-CARBOXY-3-PHENYLPROPYL)-DIPEPTIDES

BRIEF DESCRIPTION OF THE INVENTION

The N-terminal 1-carboxy-3-phenylpropylated dipeptides of this invention reduce blood pressure in animals. They function as inhibitors of angiotensin converting enzyme in that they block C-terminal cleavage of the histidyl[9]-leucine[10] dipeptide from the decapeptide angiotensin I, thereby decreasing conversion to the strong pressor octapeptide angiotensin II. Thus, the dipeptide derivatives of this invention are antihypertensive agents useful in the treatment of angiotensin II related hypertension.

DETAILED DESCRIPTION OF THE INVENTION

In accordance with this invention there is provided a group of hypotensive agents of the formula:

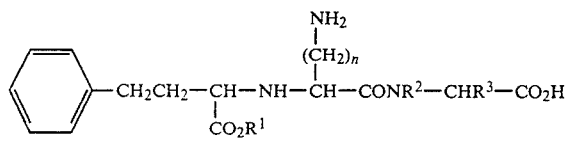

in which $R^1$ is hydrogen, alkyl of 1 to 6 carbon atoms, arylalkyl of 7 to 16 carbon atoms or aryl of 6 to 10 carbon atoms;

$R^2$ is aryl of 6 to 10 carbon atoms, 2-, 3- or 4-pyridyl, 2- or 3-thienyl, 2- or 3-indolyl, 2- or 3-furanyl, or their substituted analogues containing from one to two substituents selected from alkyl of 1 to 4 carbon atoms, arylalkyl of 7 to 10 carbon atoms, halo, alkoxy of 1 to 4 carbon atoms, hydroxyl, nitro or amino;

$R^3$ is hydrogen, alkyl of 1 to 6 carbon atoms, arylalkyl of 7 to 16 carbon atoms or aryl of 6 to 10 carbon atoms; and n is one of the integers 1, 2, 3, 4 or 5; or a pharmaceutically acceptable salt thereof.

The alkyl moieties referred to in the preceding paragraph include both straight and branched chain hydrocarbon radicals such as methyl, ethyl, propyl, isopropyl, butyl, isobutyl, tertiary-butyl, pentyl, isopentyl, hexyl and 2-ethyl-butyl. Preferably the alkyl moieties contain from one to four carbon atoms. The aryl moieties cover univalent aromatic hydrocarbon radicals such as phenyl, 1-naphthyl, 2-naphthyl, tolyl, xylyl, cumenyl, and the like. The phenyl radical is the preferred aryl group. The arylalkyl moieties embrace hydrocarbon radicals with the preceding combined meanings of the alkyl and aryl groups. By halo, applicant includes chloro, bromo, fluoro and iodo substituents.

The preferred compounds of this invention are those of the formula:

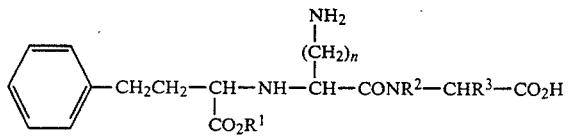

in which $R^1$ is hydrogen or alkyl of 1 to 4 carbon atoms;

$R^2$ is phenyl or substituted phenyl containing from one to two substituents selected from alkyl of 1 to 4 carbon atoms, halo, alkoxy of 1 to 4 carbon atoms, hydroxyl, nitro or amino;

$R^3$ is hydrogen or alkyl of 1 to 4 carbon atoms; and n is the integer 4; or a pharmaceutically acceptable salt thereof.

The compounds of this invention contain chiral centers at the alpha carbon atom of lysine, the carboxy substituted phenylpropyl carbon atom and when $R^3$ is other than hydrogen, at the carbon atom to which it is attached.

In each instance, the S configuration is preferred although the products in their R and R,S configuration about each chiral center are active antihypertensive agents. By selection of appropriate reactants with known steroconfiguration, the final product obtained may be limited to epimers separable by standard methods of separation such as fractional crystallization, chromatography or distillation.

The pharmaceutically acceptable salts of the acid moieties may be derived from either inorganic or organic bases to yield ammonium salts; alkali metal salts (sodium, potassiu, etc.); alkaline earth salts preferably calcium or magnesium; dicyclohexylamine salts, lower alkylamine salts; di(lower)alkylamine salts; tri(lower)alkylamine salts and the corresponding omegahydroxy analogues (e.g. methylamine, ethylamine, propylamine, dimethylamine, diethylamine, dipropylamine, trimethylamine, triethylamine, tripropylamine, dihydroxyethylamine, dehydroabietylamine, and the like). Similarly, more complex amines which are employed in depot administration for slow release into the body, such as N, $N^1$-dibenzylethylenediamine, are applicable bases for pharmaceutically acceptable salt formulation. These salts are produced conventionally by neutralization of the acidic proton of one or both of the carboxyl groups with an equivalent of the desired base.

Alternatively, acid addition salts of the basic moieties of the compounds of this invention represent pharmaceutically acceptable salts and are produced conventionally by reaction of the free base with the desired acid such as hydrochloric, hydrobromic, sulfuric, phosphoric, methane sulfonic, maleic, fumaric, succinic acids and the like. The compounds are also capable of forming internal salts.

Although numerous methods for producing the compounds of this invention are available to the chemist, the preferred method involves the conventional coupling:

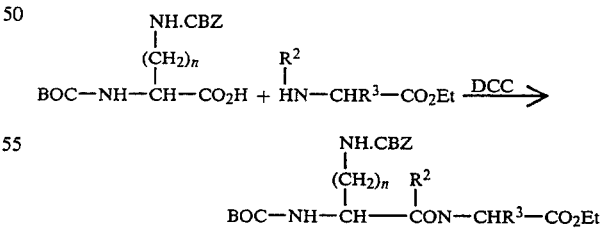

followed by hydrolysis of the ester. The resulting acid is deprotected with trifluoroacetic acid and the α-amino group is alkylated with an appropriately substituted β-keto acid, thusly:

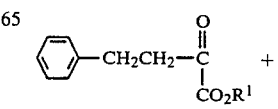

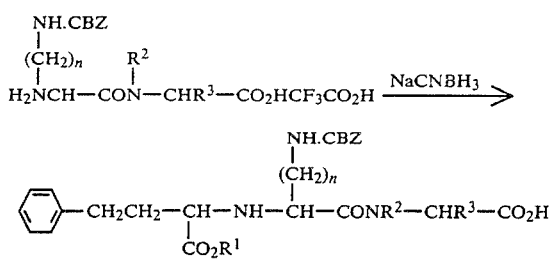

The CBZ group is then removed by hydrogenation.

The amino acids employed in the initial DCC coupling are either commercially available or are readily preparable by the medicinal chemist. The β-keto acid reactants are generally known literature compounds and are readily prepared following the technique of Meyers et al., Tetrahedron Letters, No. 47 pages 4657–4660 (1978).

The following examples illustrate the preparative technique employed in the production of the compounds of this invention.

EXAMPLE 1

$N^\alpha$-(DL-1-carboxy-3-phenylpropyl)-$N^\epsilon$-benzyloxycarbonyl-L-lysyl-N-phenylglycine N-Phenyl-glycine ethyl ester (Chemical Dynamics Co.) (10 g, 56 mmoles) was mixed with BOC-Lys(CBZ)OH (21.3 g, 56 mmoles) in methylene dichloride cooled in an ice-bath and treated with dicyclohexylcarbodiimide (11.55 g, 56 mmoles). The mixture was allowed to reach room temperature overnight, then filtered and the filtrate was washed with aq. NaHSO$_4$, H$_2$O, aq. NaHCO$_3$, brine and dried overnight over MgSO$_4$. The solvent was evaporated to afford a yellow oil, 33.25 g, containing some dicyclohexylurea (DCU).

The above crude material was subjected to column chromatography through silica gel 60 (930 g). A stepwise gradient elution was applied starting with hexane and increasing the EtOAc content to 40%, v/v, where the desired $N^\alpha$-tert-Butyloxy-carbonyl-$N^\epsilon$-benzyloxycarbonyl-L-lysyl-N-phenyl-glycine ethyl ester emerged, 13 g (43% yield). TLC silica gel 60, 254F, precoated glass plates R$_f$(EtOAc-cycloHexane, 1:1, v/v) 0.52, some DCU present at R$_f$ 0.40.

Aminoacid analysis shows the presence of lysine. Mass spectrum (C.I) M+1 542, HPLC μBondapak C$_{18}$ column (4 mm+30 cm) 50% 0.1M-NH$_4$OAc, pH 4 50% CH$_2$CN, 82% and a minor peak 18%.

NMR (CDCl$_3$) ppm 1.25 s, 1.1 m (18H), 5 s (4H), 3.9–4.8 m (5H), 7.25 d (10H).

The compound of the previous paragraph (5 g, 9.2 mmoles) was dissolved in methanol (ca. 75 ml) and treated dropwise with 1N-NaOH (13.5 ml). The reaction was allowed to proceed until no starting material was present after which time, the pH was adjusted to 3.5 and evaporated under vacuo to a small volumn. The residue was mixed with 5% aq. NaHSO$_4$ (ca. 200 ml) and extracted with ethylacetate. The organic layer was washed twice with brine then dried over MgSO$_4$ and evaporated to dryness to afford $N^\alpha$-tert-Butyloxycarbonyl-$N^\epsilon$-benzyloxycarbonyl-L-lysyl-N-phenylglycine as an oil (4 g. 84.5%).

TLC silica gel 60, 254F precoated glass plates. R$_f$ (CHCl$_3$-MeOH, 10:1, v/v) 0.23 trace at 0.63 R$_f$(CHCl$_3$-MeOH-AcOH, 85:10:5, v/v) 0.58 trace at 0.68, HPLC μBondapak C$_{18}$ column (4 mm+30 cm) 50% 0.1M-NH$_4$OAc pH 4–50% CH$_3$CN, 84% Mass spectrum (M-CO$_2$+H) 470.

The compound of the preceding paragraph (5 g, 10 mmoles) was treated with a mixture of CF$_3$CO$_2$H-CH$_2$Cl$_2$-anisole (1:1:10%) in an ice-bath for 30 minutes. The solution was evaporated to dryness and the residue was triturated with diethyl ether first and then with hexane to afford $N^\epsilon$-Benzyloxycarbonyl-L-lysyl-N-phenylglycine trifluoroacetate salt as a solid (foam) 4.6 g (87%).

HPLC μBondapak C$_{18}$ column (4 mm×30 cm) 77% 0.1M-NH$_4$OAc, pH 4–23% CH$_3$CN, 81% Mass spectrum (M-H$_2$O) 396.

2-Oxo-4-phenylbutyric acid (8.63 g) was dissolved in 40 ml H$_2$O by adjusting the pH to 6.8 with 1N-NaOH. To this solution the trifluoroacetate dipeptide salt of the preceding paragraph (4.58 g, 8.7 mmoles) was added and the pH was adjusted again to 6.8 then a solution of NaCNBH$_3$ (1.7 g, 3.1 equiv.) in water was added dropwise and the pH was kept at 6.8 with a few drops of acetic acid. The reaction mixture was stirred overnight then it was treated with 180 ml wet resin AG 50 W-×2 (H$^+$) and applied onto a column containing 200 ml of AG 50 W-×2 (H$^+$).

The column was washed with 90% aq-MeOH and then with 2% aq-pyridine followed by 5% aq-pyridine. The fractions containing the desired compound were pooled and lyophilized to yield 3.44 g of crude material. This material was applied onto a silica gel 60 column (155 g) and eluted with increasing concentrations of MeOH in CHCl$_3$(CHCl$_3$ to 25% MeOH in CHCl$_3$). The title compound emerged at 5% MeOH in CHCl$_3$. Yield 1.95 g.

TLC, silica gel 60, 254F precoated glass plates, R$_f$ (CHCl$_3$-MeOH, 2:1, v/v) 0.32.

Analysis for: C$_{32}$H$_{37}$N$_3$O$_7$.2.5H$_2$O

Calculated: C, 61.92; H, 6.82; N, 6.77

Found: C, 61.98; H, 6.10; N, 6.92

HPLC μBondapak C$^\sim$column (4 mm+30 cm) 60% 0.1M-NH$_4$OAc buffer pH 4–40% CH$_3$CN fast peak 35% slow peak 56%.

EXAMPLE 2

$N^\alpha$-(DL-1-carboxy-3-phenylpropyl)-L-lysyl-N-phenylglycine

The compound of Example 1 (1.7 g) in 70 ml of MeOH-H$_2$O (4:1, v/v) was hydrogenated in the presence of 10% Pd-C overnight. The catalyst was filtered off and the filtrate was evaporated to dryness. The residue was lyophilized to yield 800 mg of the title compound.

TLC, Silica gel 60, 254F, precoated glass plates, R$_f$ (CHCl$_3$-MeOH, 1:2, v/v) 0.01, R$_f$ (EtOAC-n-BuOH-H$_2$O-AcOH, 1:1:1:1, v/v) 0.65.

Analysis for: C$_{24}$H$_{31}$N$_3$O$_5$.2H$_2$O

Calculated: C, 60.44; H, 7.19; N, 8.81

Found: C, 60.17; H, 6.81; N, 8.67

HPLC: μBondapak C$^{18}$ Column (4 mm+30 cm) 90% 0.1M-NH$_4$OAc buffer pH 4–10% CH$_3$CN fast peak 12.5% slow peak 80%.

EXAMPLE 3

N$^\alpha$-(DL-1-carboxy-3-phenylpropyl)-L-lysyl-N-p-methoxyphenylglycine

The title compound was prepared following the procedure of Examples 1 and 2, starting from N-p-methoxylphenyglycine ethyl ester.

TLC, Silica gel 60, 254F, precoated glass plates, R$_f$ (EtOAc-n-BuOH-H$_2$O-AcOH, 1:1:1:1, v/v) 0.68

Analysis for: C$_{25}$H$_{39}$N$_3$O$_9$.3H$_2$O
Calculated: C, 57.13; H, 7.48; N, 7.99
Found: C, 57.04; H, 6.39; N, 7.72

HPLC µBondapak C$^{18}$ Column (4 mm×30 cm) fast peak 16%, slow peak 82%.

Following the procedure of the preceding examples while employing the reactants as follows affords the named N-(1-carboxy-3-phenylpropyl)dipeptide:

Compound 3

β-Keto ester-2-Oxo-4-phenylbutyric acid ethyl ester
N-Terminal A.A.-L-Lysine
C-Terminal A.A.-N-p-chlorophenyl-glycine
Product-N$^2$-[DL-1(ethoxycarbonyl]-3-phenylpropyl]-L-Lysyl-N-p-chlorophenylglycine

Compound 4

β-Keto ester-2-Oxo-4-phenylbutyric acid phenylmethyl ester
N-Terminal A.A.-L-2,3-diaminopropionic acid
C-Terminal A.A.-N-(2-Indolyl)-L-phenylalanine
Product-N$^2$-[DL-1(phenylmethoxycarbonyl)-3-phenylpropyl]-L-2,3-diaminopropionyl-N-(2-indolyl)-L-phenylalanine

Compound 5

β-Keto acid-2-Oxo-4-phenylbutyric acid
N-Terminal A.A-L-Lysine
C-Terminal A.A.-N-(2-pyridyl-L-alanine
Product-N$^2$-(DL-1-carboxy-3-phenylpropyl)-L-lysyl-N-(2-pyridyl)-L-alanine

Compound 6

β-Keto ester-2-Oxo-4-phenylbutyric acid phenyl ester
N-Terminal A.A.-L-Lysine
C-Terminal A.A.-N-(2-furanyl)-L-phenylglycine
Product-N$^2$-[DL-1(phenoxycarbonyl)-3-phenypropyl]-L-lysyl-N-(2-furanyl)-L-phenylglycine

Compound 7

β-Keto acid-2-Oxo-4-phenylbutyric acid
N-Terminal A.A.-L-Lysine
C-Terminal A.A.-N-2,6-dimethyphenyl-glycine
Product-N$^2$-(DL-1-carboxy-3-phenylpropyl)-L-lysyl-N-(2,6-dimethylphenyl)glycine

Compound 8

β-Keto acid-2-Oxo-4-phenylbutyric acid
N-Terminal A.A.-L-2,4-diamino-butyric acid
C-Terminal A.A.-N-p-aminophenyl-L-alanine
Product-N$^2$-(DL-1-carboxy-3-phenylpropyl-L-2,4-diamino-butyryl-N-p-aminophenyl)-L-alanine Proper protection and deprotection of functional side chains and the α-amino group of the amino acids employed in the synthesis of the compounds of this invention is well within the skill of the chemist.

The compounds of this invention inhibit the conversion of angiotensin I to angiotensin II, thereby alleviating hypertension caused by the strong pressor action of the latter octapeptide. The compounds are administered to the hypertensive animal in single or divided doses, orally or parenterally, at a dose from about 25 to 200 milligrams per kilogram per day. The preferably oral dosing regimen provides from about 50 to 150 milligrams per kilogram per day, depending upon the severity of the hypertensive state. Oral administration in solid form by tablet or capsule may be accomplished with the compounds of this invention in neat or pure form alone or in combination with conventional adjuvants. Similarly, parenteral administration may be accomplished with physiological saline or via suspension with conventional vehicles. In any event, the dosing regimen must be individualized by the attending physician or veterinarian for the patient based upon the severity of the dysfunction.

The activity of the compounds of this invention was established by incubation of hippuryl-L-histidyl-L-leucine at 37° C. with angiotensin converting enzyme by the following procedure:

A crude angiotensin converting enzyme supernatant is obtained by blending 1 gm. of rabbit lung acetone powder (PelFreez Biologicals) with 35 ml. of 50 mM (buffered) potassium phosphate, pH 8.3 and centrifuging for 45 min. at 40,000×g.

The specific angiotensin converting enzyme substrate Hippuryl-L-histidyl-L-leucine (HHL-Sigma Chem. Co.) is prepared at 5 mM in 200 mM potassium phosphate buffer containing 757 mM NaCl at pH 8.3.

Incubation for the assay of HHL hydrolysis by angiotensin converting enzyme is carried out in a 37° C. gyrorotary incubator in disposable 13×100 mm tubes. Each 0.25 ml assay mixture contains the following components at the final concentrations: potassium phosphate buffer, 100 mM; NaCl, 300 mM; HHL, 5 mM; and enzyme 0.15 ml (10 mU approx.) added last to initiate the reaction. Zero time controls have 0.25 ml of 2N HCl added before the enzyme. The timed reactions are terminated with acid at 30 min. similarly and the hippuric acid freed from substrate is extracted into 1.5 ml of ethyl acetate layer is transferred to a clean tube. These aliquots are evaporated to dryness by heating (120° C.) in a Temp-Block module heater.

The hippuric acid is resuspended in 1.0 ml of water, the absorbance at 288 nm is determined, and the amount present is calculated from a standard curve. The amount of hippuric acid × 1.1 (extraction coefficient) × 1.5 (ratio of volumes)×1 βM hippuric acid/200 µg×1/30 min.=nM hippuric acid released/min. Enzyme activity in the presence of an inhibitor is compared with control activity, and reported as a percentage inhibition. (Cushman, D. W. and Cheung, H. S., Biochem. Pharmacol. 20 1637 (1971).

The product of Example 2 demonstrated an IC$_{50}$ of 14.6×10$^{-8}$M.

Both the products of Examples 2 and 3 were shown to reduce systolic blood pressure in male spontaneously hypertensive rats by oral administration of the compounds to groups of four rats. Blood pressures were read prior to drug administration and at 1.5, 4 and 24 hours thereafter using a Decker Caudal Plethysmograph. The results of the study are as follows:

| Compound | Dose mg/kg | Route | Hours | Blood Pressure mmHg |
|---|---|---|---|---|
| — | — | PO | 1.5 | 231 |
| Example 2 | 150 | PO | 1.5 | 196 |

-continued

| Compound | Dose mg/kg | Route | Hours | Blood Pressure mmHg |
|---|---|---|---|---|
| | 150 | PO | 4 | 194 |
| — | — | PO | 1.5 | 188 |
| Example 3 | 50 | PO | 1.5 | 183 |
| | 50 | PO | 4 | 181 |
| | 50 | PO | 24 | 204 |

What is claimed is:

1. A compound of the formula:

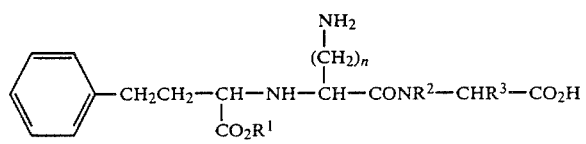

in which $R^1$ is hydrogen or alkyl of 1 to 4 carbon atoms;
$R^2$ is phenyl or substituted phenyl containing from one to two substituents selected from alkyl of 1 to 4 carbon atoms, halo, alkoxy of 1 to 4 carbon atoms, hydroxyl, nitro or amino;
$R^3$ is hydrogen or alkyl of 1 to 4 carbon atoms; and
n is the integer 4; or a pharmaceutically acceptable salt thereof.

2. The compound of claim 1 which is $N^\alpha$-(DL-1-carboxy-3-phenylpropyl)-L-Lysyl-N-phenylglycine.

3. The compound of claim 1 which is $N^\alpha$-(DL-1-carboxy-3-phenylpropyl)-L-lysyl-N-p-methoxyphenylglycine.

4. The compound of claim 1 which is $N^2$-(DL-1-carboxy-3-phenylpropyl)-L-lysyl-N-(2,6-dimethylphenyl)glycine.

5. The compound of claim 1 which is $N^2$-(DL-1-carboxy-3-phenylpropyl)-L-2,4-diamino-butyryl-N-p-aminophenyl)-L-alanine.

* * * * *